United States Patent [19]

Joh

[11] Patent Number: 4,872,867
[45] Date of Patent: Oct. 10, 1989

[54] COMPOSITIONS HAVING ANTITHROMBOGENIC PROPERTIES AND BLOOD CONTACT MEDICAL DEVICES USING THE SAME

[75] Inventor: Yasushi Joh, Yokohama, Japan

[73] Assignee: UBE Industries, Ltd., Ube, Japan

[21] Appl. No.: 317,108

[22] Filed: Feb. 28, 1989

Related U.S. Application Data

[63] Continuation of Ser. No. 33,157, Jan. 30, 1987, abandoned.

[30] Foreign Application Priority Data

Jun. 19, 1985 [JP] Japan ................................. 60-133194
Jun. 19, 1985 [JP] Japan ................................. 60-133195

[51] Int. Cl.$^4$ ............................................ A61M 5/005
[52] U.S. Cl. ..................................... 604/269; 623/11; 523/113
[58] Field of Search ............... 604/265, 266, 269, 289; 514/822; 427/2; 523/112, 113; 525/103, 931; 623/1, 11

[56] References Cited

U.S. PATENT DOCUMENTS

| | | | |
|---|---|---|---|
| 3,746,683 | 7/1973 | Salyer et al. | 523/112 |
| 3,887,483 | 6/1975 | Morehouse | 521/112 |
| 4,113,690 | 9/1978 | Lewis | 524/266 |
| 4,144,216 | 3/1979 | Clark et al. | 524/356 |
| 4,192,827 | 3/1980 | Mueller et al. | 525/123 |
| 4,211,729 | 7/1980 | Marquardt et al. | 528/32 |
| 4,265,233 | 5/1981 | Sugitachi et al. | 128/156 |
| 4,322,518 | 3/1982 | Blizzard | 427/387 |
| 4,345,053 | 8/1982 | Rizk et al. | 524/588 |
| 4,371,686 | 2/1983 | Yamamoto et al. | 528/62 |
| 4,467,081 | 8/1984 | Chang et al. | 524/859 |
| 4,548,990 | 10/1985 | Mueller et al. | 525/123 |
| 4,557,724 | 12/1985 | Gregonis et al. | 604/265 |
| 4,578,077 | 3/1986 | Joh | 128/1 R |
| 4,604,412 | 8/1986 | Joh et al. | 523/116 |
| 4,675,361 | 6/1987 | Ward, Jr. | 523/112 |
| 4,686,137 | 8/1987 | Ward, Jr. et al. | 525/403 |

FOREIGN PATENT DOCUMENTS 12069 1/1985 Japan.

*Primary Examiner*—C. Fred Rosenbaum
*Assistant Examiner*—Sharon Rose
*Attorney, Agent, or Firm*—Frishauf, Holtz, Goodman & Woodward

[57] ABSTRACT

This invention is a composition having anti-thrombogenic properties, comprising as essential constituent components a polyurethane or polyurethane urea containing polytetramethylene oxide in its main chain, a water soluble and/or water swellable macromolecules, and a silicon-containing compound capable of forming polysiloxane while crosslinking; and a blood contact medical device having such a composition on blood contact surfaces. According to this invention, it is possible to provide on blood contact surfaces a hydrophilic polymer which is excellent in dynamic properties and very rich in the antithrombogenic properties, and the invention can be greatly contributory in the field of blood contact medical devices.

14 Claims, No Drawings

COMPOSITIONS HAVING ANTITHROMBOGENIC PROPERTIES AND BLOOD CONTACT MEDICAL DEVICES USING THE SAME

This application is a continuation of application Ser. No. 07/033,157, filed Jan. 30, 1987, now abandoned, which is the U.S. designated application of PCT/JP86/00309 filed June 18, 1986.

BACKGROUND OF THE INVENTION

This invention relates to a novel composition having antithrombogenic properties and a novel blood contact medical device, and, more particularly, to a novel composition comprising antithrombogenic properties, basically comprising polyurethanes, and a blood contact medical device comprising blood contact surfaces formed by the composition.

DESCRIPTION OF THE PRIOR ART

Known antithrombogenic elastomers have hitherto included polyether type segmented polyurethanes (e.g., Biomers produced by Ethicon Inc., U.S.A.), silicone resins, or a block copolymer of polysiloxane and polyurethane (e.g., Cardiothane produced by Kontron Inc. U.S.A.), heparinized polyurethanes (Patent Publication No. 13729/1980), etc. These elastomers have still insufficient antithrombogenic properties from a practical viewpoint. For example, the segmented polyurethanes have been required to be further improved, or the heparinized polyurethanes, from which heparin may flow out and lose their antithrombogenic properties in short time. Also, there are required cumbersome forming processes in the synthesis and sterilization as long as they employ physiologically active heparins, this results in high production cost. Also, a block copolymer comprising polysiloxane and polyurethane having silicon to nitrogen bonds (U.S. Pat. No. 3,562,352) is a reactive substance capable of crosslinking. Along with its poor stability with time, antithrombogenic properties may vary greatly depending on the preservation conditions and the shaping conditions. Accordingly, blood contact surfaces with constant and excellent antithrombogenic properties can hardly be obtained even if the production process is severly controlled.

Among the segmented polyurethanes, a hydrophilic polyurethane wherein a soft segment in a main chain comprises, for example, a polyethylene oxide, has an excellent antithrombogenic property. Because of the hydrophilic nature, however, once it contacts with blood, it may absorb water in blood to swell and cause changes in volume, or may sometimes partly dissolve in water to drastically reduce its mechanical properties. Thus, it can not be used practically. Elastomers with desirable mechanical properties are essential to develop the blood contact medical devices, nevertheless there have been no such materials as yet. The development of such materials have long been required.

DESCRIPTION OF THE INVENTION

Objects of this invention are firstly to provide a composition with excellent antithrombogenic properties and good mechanical properties, and secondly to provide a blood contact medical device having blood contact surfaces of such a composition.

The objects and characteristic features of this invention will be understood from the following description.

The objects of this invention can be achieved with a composition having antithrombogenic properties, comprising as essential constituent components a polyether type polyurethane or polyurethane urea containing in its main chain a segment comprising polytetramethylene oxide, a water soluble polymer and/or water swellable polymer, and a silicon-containing compound capable of being activated by water and induce the condensation polymerization with crosslinkings to form polysiloxane; and a blood contact medical device characterized in that it comprises a blood contact surface which is constituted of a polyurethane or polyurethane urea having polytetramethylene oxide in its main chain, a water soluble and/or water swellable polymer, and a polysiloxane having a crosslinked structure.

The present inventors have remarked the fact that a hydrophobic polyether segmented polyurethane having polytetramethylene oxide in its molecular chain has excellent mechanical strength, and have made intensive studies this polyurethane hydrophilic without reducing the mechanical strength. As a result, it was found that, in a method of blending a hydrophobic polyurethane whose polyether segment is polytetramethylene oxide and a hydrophilic polyurethane whose polyether segment is a polyalkylene oxide (wherein the carbon atom number of alkylene is 2 and/or 3), the mechanical strength can not be improved even if the blending proportion and the blending method are widely varied.

The present inventors have also found that a hydrophilic polyurethane, especially, a polyether type polyurethane having a soft segment comprising a polyethylene oxide or a polypropylene oxide, has excellent antithrombogenic properties, and, in particularly, a polyurethane having a soft segment of the polyethylene oxide has outstanding antithrombogenic properties.

However, as already mentioned, it has been confirmed that it has poor mechanical strength because of its water absorbency and water solubility. Upon contact with water dynamic properties are decreased, or may partly dissolve in water, therefore it can not be use practically.

The present inventors have succeeded in developing an excellent antithrombogenic material basically comprising polyurethane, by a very unique method.

This invention is constituted of an essential component (a first component) comprising a polyether type segmented polyurethane having polytetramethylene oxide in its main chain which is excellent in dynamic property, and a second component comprising a water soluble polymer and/or a water swellable polymer which is/are soluble in a solvent commonly used for the first component, and further a third component comprising a crosslinkable silicon-containing compound capable of being activated with water and forming a polysiloxane by condensation reactions. A surface formed by being coated with the composition containing these three components was found to be stable and excellent in the antithrombogenic properties. The present invention has thus been accomplished.

It has become clear that, when coated with a mixture of only the first component and the second component of the composition of this invention, the first component and the second component undergo phase separation at the stage of forming, with the result that the second component comes up to the surface and flows away upon contact with water. In such a method, excellent antithrombogenic properties can be exhibited at an initial stage where chains of the water soluble polymers and/or water swellable polymers having good anti-thrombogenic properties are present in a large quantity on the blood contact surfaces, but they flow out in a short time to decrease effect. Moreover, although the water soluble polymer flowed out into blood can be metabolized, it may be not preferred that it moves into blood circulation in large amount.

The present inventors have found that when the above-mentioned crosslinkable silicon-containing compound capable of being activated by water is added as a third component, serves as if it is a solvent in the mixed compostion because of its low molecule weight, and had an idea to utilize this. Namely, considering a case where the first component and the second component are dissolved in a solvent, for example, in tetrahydrofuran, the crosslinking silicon-containing compound of the third component can well dissolve in tetrahydrofuran. Thus it can be understood the system works as if the first component and the second component have been dissolved in a mixed solvent comprising tetrahydrofuran and the silicon-containing compound.

The third component of this invention, is not a polymer but a monomer (monomeric substance) or an oligomer, i.e., the silicon-containing compound capable of being activated by water and condensed with crosslinking reaction to form polysiloxane, is not a polymer but a monomer (monomeric substance) or an oligomer, and, in order to form a polysiloxane having network structure, employs as an essential component, a low molecular silicon-containing compounds that can produce 3 or more crosslinkable functional groups (hydroxyl groups) by activation treatment.

The silicon-containing crosslinking agent herein mentioned refers to a compound having one or more of silicon atoms in the molecule and having a functional group that can give a crosslinkability by a suitable procedure for activation, and, specifically, compounds which are known as room temperature vulcaniser or silane coupling agents for silicone rubbers or silicone resins.

As these silicon-containing crosslinking agents, preferably used are those having a functional group that can be activated by water. Typical examples thereof include Si—OCOR, Si—OR (R is hydrocarbon radical such as $CH_3$, $C_2H_5$, $C_3H_7$ and $C_4H_9$), Si—OX, SiX (X is halogen such as Cl and Br), Si—$NR_2$ (R is same as above), etc. The resulting silicon-containing polymer formed from such silicon-containing crosslinking agent is in the form of polysiloxane structure.

Examples of the silicon-containing crosslinking agent, which exhibit crosslinkabilities by activation by water, having one silicon atom in the molecule to form a polysiloxane may include the compounds represented by the general formula:

wherein R represents a hydrocarbon radical such as an alkyl group and an aryl group; R' represents an alkoxy group, an acyloxy group, a halogen atom or an amine radical; and n represents 0 or 1.

As these silicon-containing crosslinking agents, widely used are known room temperature crosslinking type silane coupling agents, including, for example, all the silicon-containing crosslinking agents described in a catalogue "Silicon Compounds, Register & Review" ©(1979) published by Petrarch System Inc. or "Silicones" ©(1981) published by the same company.

Specific examples may include, for example, methyltriethoxysilane, methyltriacetoxysilane, tetramethoxysilane, tetraacetoxysilane, etc.

When blood contact surfaces of a blood contact medical device are formed using the composition of this invention, the silicon-containing compound is activated by the action of moisture, or water, in the atmosphere along with evaporation of the solvent to cause a condensation reaction accompanied with crosslinking.

With the evaporation of the solvent, each of the first, second and third components becomes gradually high in their concentrations, and the same components show tend to aggregate each other to develop micro phase separation, but the silicon-containing compounds uniformly distributed in the state close to the molecular dispersion mutually repeat condensation polymerizations accompanying crosslinkings, to form hydrophobic polysiloxanes.

During the course of the above reactions, while the crosslinked polysiloxanes form aggregates with each other, the first component polyurethane having relatively hydrophobic polytetramethylene chains and also the second hydrophilic component, water soluble polymer and/or water swellable polymer are entangled together to form interpenetrating polymer networks.

Accordingly, the relatively hydrophobic polyether type polyurethane having polytetramethylene oxide in its soft segments (the first component) and the water soluble and/or water swellable polymers soluble in an organic solvent commonly used for the above first component (the second component) are both entangled together in the highly hydrophobic crosslinked polysiloxane (the third component) to form interpenetrating polymer network structure. This structure shows the hydrophobic-hydrophilic micro heterogeneous structure which exceedingly resembles to an organism.

The present inventors discovered that the second component swells upon contact with blood to cover the blood contact surfaces while widely hydrating the same, but attaining the state that it does not dissolve out, and, in addition, the hydrophilic polymer selectively effects preferential adsorption of albumin in blood to turn the blood contact surfaces into quasi-living organisms, whereby the formation of thrombi can be effectively suppressed.

The second component water soluble and/or water swellable polymers used in this invention are required to have a solvent commonly used for the first component, in other words, to dissolve in the solution of the first component.

These polymers may include macromolecules having a polyalkylene oxide (wherein number of alkylene carbon atom is 2 and/or 3) in the main chain, for example, polyether type polyurethanes having a segment comprising the same, and specifically, macromolecules such as polyethylene oxide, polypropylene oxide, an ethylene oxide/propylene oxide random copolymer, a polyethylene oxide/polypropylene oxide block copolymer (of A-B type, A-B-A type, B-A-B type etc.), or, alternatively, they may be polyether type segmented polyurethanes or polyurethane ureas containing a soft segment. Besides these, preferably used are polyvinyl alcohol, polyvinyl pyrrolidone, polyacrylic acid (or a salt thereof), polyhydroxyethyl acrylic acid (or a salt thereof), atelo collagen, water soluble gelatin, chondroitin sulfuric acid (or a salt thereof), hyaluronic acid, alginic acid, water soluble starch, oxydized starch (dialdehyde starch), diacetone acrylamide, 2-acrylamide-2-methylpropane sulfonic acid (or a salt thereof), soluble heparin, etc. These may be used alone or as a mixture.

These water soluble and/or water swellable polymers are very hydrophilic nature when used alone, and extremely swell by water absorption upon contact with water. They are partly soluble in water and have very poor dynamic properties. However, the present inventors found the effects that, when they are used as a component of the composition according to this invention, they show almost the same dynamic properties as the first component; hydrophobic polyurethane, and, on the other hand, segments of hydrophilic polyalkylene oxide can be exposed on the blood contact surfaces to exhibit outstanding anti-thrombogenic properties.

The second component in this invention may include polyethylene glycol, polypropylene glycol, as well as a block copolymer and random copolymer of polyethylene glycol with polypropylene glycol, or may include a polydimethyl siloxane/polyethylene glycol block copolymer, polydimethyl siloxane/polyethylene glycol copolymer, or a polyurethane containing a block copolymer in its soft segments.

When this second component have a common segment to the first component and the third component, it can give particularly good mixing state and form the interpenetrating polymer network structure desirably. For example, a polyurethane having polyethylene glycol as a soft segment (there can be one having the molecular structure common to the first component) or a polydimethyl siloxane/polyethylene glycol copolymer (there can be one having the molecular structure common to the third component) may be exemplified.

The weight ratio of the first component to the second component of this invention (first component/second component) may range between 0.5 and 20, preferably between 1.0 and 10.0. The ratio less than 0.5 may result in poor dynamic properties endurable enough for practical use, and the ratio more than 20 may result in no expectancy in the antithrombogenic effects.

The weight ratio (calculated in terms of polysiloxane) of the second component to the third component (second component / third component) may range between 20.0 and 0.05, preferably between 10.0 and 0.1, more preferably between 5.0 and 0.2. A ratio larger than 20.0 may possibly cause the dissolving-out of the water soluble polymer in water, a the ratio smaller than 0.05 may result in poor antithrombogenic effect, whereupon the effect of this invention can not be sufficiently exhibited.

The polyurethane, the first component used in this invention, may be replaced with polyurethane urea obtained by preparing a prepolymer of polytetramethylene glycol with, for example, 4,4'-diphenylmethanediisocianate, followed by chain extension of the prepolymer by use of ethylenediamine or hexamethylenediamine, or a polyurethane obtained by using a diol, for example, ethylenediol or butanediol as a chain extender.

The polytetramethylene glycol used in this invention may have a molecular weight of 400 to 3,000, preferably 1,000 to 2,000. A molecular weight less than 400 may result in too hard polyurethane, having insufficient antithrombogenic properties, and the molecular weight more than 3,000 may cause the lowering of dynamic properties of the resulting polyurethane, undesirably.

The isocyanate for synthesizing the polyurethane used in this invention may include, in addition to the above-mentioned, diisocianates conventionally used for the production of polyurethanes, for example, 1,4-phenylenediisocyanate, 4,4'-dicyclohexylmethanediisocyanate, tetramethylenediisocyanate, hexamethylenediisocyanate, 2,4-tolylenediisocyante, 2,6-tolylenediioscyanate, cyclohexane-1,4-diisocyanate, a mixture of 2,4-tolylenediisocyanate with 2,6-tolylenediisocyanate, xylilenediisocyanate, 1,3-phenylenediisocyanate, naphthalene-1,5-diisocyanate, etc., which can be used alone or as a mixture.

As the chain extender, there may be used chain extenders having an active hydrogen group capable of reacting with a bifunctional isocyanate group, for example, aliphatic diamines such as ethylenediamine, propylenediamine, butylenediamine and hexamethylenediamine; alicyclic, aromatic acid diamines such as cyclohexanediamine, piperadine and xylenediamine; aromatic diamines such as tolylenediamine, phenylenediamine and 4,4'-diphenylmethanediamine; hydrazines; glycols such as ethylene glycol and 1,4-butanediol; and water; etc.

The polyurethane thus synthesized may be used in the form of a synthetic solution, or by precipitating the resulting polyurethane with a precipitant, for example, water, alcohol or the like, carrying out sufficient washing with water or ethanol, and optionally repeating again the precipitation to remove impurities, followed by drying.

The composition of this invention, containing the polyurethane, can be used as a solution by coating, dipping or spraying to form blood contact portions in a blood contact medical device. This composition is very stable even when it is preserved in the solution and is easy to handle, and has excellent properties that exhibits the antithrombogenic properties with good reproducibility.

As for the dynamic properties of a film formed by this composition, elongation ranges 300 to 500 % or more, a tensile resistance ranges 100 to 500 $kg/cm^2$, showing excellent mechanical properties.

The formed film comprising the composition obtained by using polyurethane as a basic component, to which the water soluble polymer and/or the water swellable polymer are added, and forming these polymers into a interpenetrating polymer network structure by using the crosslinking polysiloxane, can retain dynamically sufficient properties even upon contact with water, and also, at the interface with water, the water soluble polymer and/or water swellable polymer can hydrate, swell, and preferentially and selectively adsorb albumin from blood, turning the blood contact surfaces into quasi-living organisms, thereby exhibiting outstanding antithrombogenic properties.

From these results, an antithrombogenic elastomer obtained from the composition of this invention has excellent dynamic properties and also high anti-thrombogenic properties, therefore can be desirably used for blood contact surfaces of medical devices which directly contact with blood. Specific uses thereof may include artificial hearts, pumping chambers for assist circulation devices, balloon pumps, extracorporeal circulation circuits for assist circulation devices such as artificial livers and artificial heart lung, blood bags, blood bypass pumps, catheters, etc.

BEST MODE FOR CARRYING OUT THE INVENTION

This invention will be described below specifically with reference to Examples, but by no means limited to these. In each Example, "part(s)" refers to "part(s) by weight".

EXAMPLE-1

Preparation of the First Component

Using polytetramethylene oxide having a molecular weight of 1,600, this was reacted with 4,4'-diphenylmethanediisocyanate to make a prepolymer, which was then chain extended by use of butanediol to prepare a polyether type segmented polyurethane according to a conventional method. This polyurethane was purified by re-precipitation three times in a tetrahydrofuran/methanol system.

Preparation of the Second Component

Following the preparation of the first component, except that polyethylene glycol having a molecular weight of 800 was used in place of polytetramethylene oxide used in the preparation of the first component, prepared was polyurethane having soft segments constituted of polyethylene oxide, which was then purified according to a conventional method to produce the second component.

Into 100 parts of purified tetrahydrofuran, the first component and the second components were mixed in the proportion of 9 parts and 3 parts, respectively. To this mixture, 10 parts of a methyltriacetoxysilane/ dimethyldiacetoxysilane (2:8) mixture were added and thoroughly stirred to give a homogeneous solution. The solution was coated in a test tube having an inner diameter of 13 mm, and allowed to stand 2 weeks at room temperature in an atmosphere of 65 % RH to complete the condensation of silicone components. Using this, a Lee-White test was carried out to find that it took 89 minutes until blood clotted.

On the other hand, in a glass test tube, the coagulation time was 11 minutes. In a control coated with only the first component, the clotting time was 47 minutes.

The same solution was cast on a glass plate to prepare a film, and tensile strength and breaking extension thereof were determined to find that they were 0.69 kg/mm and 650 %, respectively. In water of 20° C., these values were 0.51 kg/mm and 780 %, respectively.

EXAMPLE-2

Using polyvinyl chloride containing a plasticizer, a sack type blood pump having an internal volume of 70 ml was produced. In the sack portion of this pump, the content of the plasticizer (dioctylphthalate) was 74 parts based on 100 parts of polyvinyl chloride. On the inner wall of this blood pump, the three components-containing antithrombogenic elastomer solution prepared in Example-1 was applied, dried at room temperature in an atmosphere of 65 % RH, and allowed to stand for 20 days to complete condensation and crosslinking of polysiloxane.

This blood pump was used as a ventricular assist pump ventricle to a goat, and tested for 4 weeks at an output of as low as 1 lit/min to reveal that no thrombus was observed at all in the blood pump.

On the other hand, in a control where only the first component was applied, thrombi were seen partially in the sack portion in 5 days under the same conditions.

EXAMPLE-3

Into 100 parts of purified tetrahydrofuran, the first component prepared in Example-1 and polyvinyl pyrrolidone (molecular weight: 24,000) as the second component were mixed in the proportion of 9 parts and 2 parts, respectively. To this mixture, 10 parts of a methyltriacetoxysilane/dimethylacetoxysilane mixture (3:7) were added as the third component, and the resulting mixture was thoroughly stirred to make a homogeneous solution. This solution was coated in a test tube having an inner diameter of 13 mm, and allowed to stand for 2 weeks at room temperature in an atmosphere of 65 % RH to complete condensation of silicone components. Using this, a Lee-White test was carried out to find 95 minutes until blood clotted.

On the other hand, in a glass test tube, the clotting time was 11 minutes. In a control coated with only the first component, the clotting time was 47 minutes.

The same solution was casted on a glass plate to prepare a film, and tensile strength and breaking extension thereof were determined to find 0.62 kg/mm and 624 %, respectively. In water of 20° C., these values were 48 kg/mm and 790 %, respectively.

EXAMPLE-4

A sack type blood pump having an internal volume of 70 ml was produced using polyvinyl chloride. In a sack portion of this pump made of polyvinyl chloride, the content of a plasticizer (dioctylphthalate) was 73 parts based on 100 parts of polyvinyl chloride. On the inner wall of this blood pump, the three component-containing antithrombogenic elastomer prepared in Example-3 was coated, dried at room temperature in an atmosphere of 65 % RH, and allowed to stand for 20 days to complete condensation and crosslinking of polysiloxane.

This blood pump was used as a ventricular assist pump ventricle to a goat, and tested for 1 month at an output of as low as 0.8 lit/min to reveal that no thrombus was seen at all in the blood pump.

EXAMPLE-5

The first component was synthesized in the same manner as in Example-1 except that dimethyl sulfoxide was used as a solvent for preparing the first component and ethylene diamine was used as a chain extender. The resultant polyurethane had the structure of polyurethane urea. Synthesis of the second component in this Example was carried out in the same manner as that of the second component in Example-1 except that an ethylene glycol/propylene glycol copolymer (molecular weight: 650) was used and dimethyl sulfoxide was used as a solvent for the preparation.

The first component and the second component were purified according to a conventional method.

In 100 parts of dimethylacetamide, the first component and the second component were dissolved in the proportion of 10 parts and 3 parts, respectively, and, to the solution, 5 parts of a 6:4 mixture of dimethyldiethoxysilane and methyltriethoxysilane were added to make a homogeneous solution.

This solution was coated in the interior of a polyvinyl chloride tube (with tapered both ends) having a full length of 30 cm, and allowed to stand in an atmosphere of 65 % RH to sufficiently effect condensation and crosslinking of polysiloxane.

Using an adult filial dog having a weight of 10 kg, the above tube was inserted between the central side of one femoral artery and the peripheral side of another femoral artery to produce an extracorporeal bypass. Bypassing was carried out at a blood flow of 20 to 70 ml/min for 12 hours to examine deposit of thrombi. As a result, there was seen no thrombus formed. A scanning electron microscope photograph of the surface showed very small adsorption of platelets.

On the other hand, in a control example where non-coated polyvinyl chloride tube having the same shape, there were seen an appreciate amount of thrombi, and a scanning electron microscope photograph also showed adsorption of large quantity of platelets, most of which produced pseudopodia and had broken shapes.

EXAMPLE-6

The first component was synthesized in the same manner as in Example-1 except that dimethyl sulfoxide was used as a solvent for preparing the first component and ethylene diamine was used as a chain extender. The resultant polyurethane had the structure of polyurethane urea.

As the second component in this Example, a mixture (1:1) of polyvinyl pyrrolidone (molecular weight of 24,000) and polyethylene glycol (molecular weight: 2,000) was used.

The first component was purified according to a conventional method.

In dimethylacetamide, the first component and the second component were dissolved in the proportion of 10 parts and 3 parts, respectively, and, to the solution, 5 parts of a 6:4 mixture of dimethyldiethoxysilane and methyltriethoxysilane were added to make a homogeneous solution.

The solution obtained was coated in the interior of a polyvinyl chloride tube (with tapered both ends) having a full length of 30 cm, and allowed to stand in an atmosphere of 65 % RH to sufficiently effect condensation and crosslinking of polysiloxane.

Using an adult filial dog having a weight of 14 kg, the above tube was inserted between the central side of one femoral artery and the peripheral side of another femoral artery to make an extracorporeal bypass. Bypassing was carried out at an average blood flow of 50 ml/min for 12 hours to examine deposit of thrombi. As a result, there was seen no thrombus formed. A scanning electron microscope photograph of the surface showed very small adsorption of platelets.

EXAMPLE-7

Polytetramethylene oxide having a molecular weight of 1,800 was reacted with 4,4'-diphenylmethylenediisocyanate to make a prepolymer, and the prepolymer was chain extended using butanediol to prepare polyurethane (the first component).

As the second component, a mixture (9:1) of polyethylene glycol having a molecular weight of 20,000 and polyethylene glycol having a molecular weight of 600 was used.

In 100 parts of a mixture (3:1) of anhydrous tetrahydrofuran and dioxane, 10 parts of the first component and 3.5 parts of the second component were dissolved to make a homogeneous solution.

To this solution, 7 parts of a mixture (8:2) of dimethyldiacetoxysilane and tetraacetoxysilane were added as the third component, and the resulting mixture was sufficiently stirred to make a homogeneous solution. To this solution, 1 part of water was added, and the mixture was kept stirring at 25° C. for 3 days. The system had apparently no change, and stood a homogeneous solution.

The solution obtained was coated in a test tube, which was kept in an atmosphere of 65 % RH for 10 days, and, after completion of crosslinking and condensation of polysiloxane, a Lee-White test was carried out to find the clotting time of 95 minutes.

In a glass test tube of a control, the coagulation time was 11 minutes.

EXAMPLE-8

The solution obtained in Example-7 was coated in the inner surface of a soft polyvinyl chloride tube with tapered both ends (containing as a plasticizer 70 % by weight of dioctylphthalate (based on polyvinyl chloride)), and allowed to stand at room temperature until the crosslinking of polysiloxane was sufficiently completed.

Using an adult filial dog, the above tube was inserted to the left open chest, between the central side of thorax descending aorta and the peripheral side thereof to produce an extracorporeal bypass. Blood flow rate was 80 ml/min, and blood flow bypassing was carried out for 3 days. In the tube of this Example, there was seen no thrombus formed at all. An electron microscopic observation also found only slight adsorption of platelets.

On the other hand, the similar test was carried out using a polyvinyl chloride tube without being coated with the solution of this Example to find that the great quantity of thrombi.

EXAMPLE-9

In 100 parts of anhydrous dimethylformamide, 10 parts of the first component obtained in Example-7 and 0.6 part of atelo collagen as the second component were dissolved to make a homogeneous solution. To this solution, 4 parts of a mixture (8:2) of dimethyldiacetoxysilane and tetraacetoxysilane were added, and the resulting mixture was sufficiently stirred to make a homogeneous solution. To this solution, 5 parts of water were added, and the mixture was kept stirring at 25° C. for 3 days. The system was visually no change, and remained as a homogeneous solution.

The solution obtained was coated in a test tube, which was kept in an atmosphere of 65 % RH for 10 days, and, after completion of crosslinking and condensation of polysiloxane, a Lee-White test was carried out to find the clotting time of 95 minutes.

In a glass test tube as a control, the clotting time was 11 minutes.

EXAMPLE-10

The solution obtained in Example-9 was coated on the inner surface of a soft polyvinyl chloride tube with tapered both ends (containing as a plasticizer 70 % by weight of dioctylphthalate (based on polyvinyl chloride)), and allowed to stand at room temperature until the crosslinking of polysiloxane was sufficiently developed.

Using an adult filial dog, the above tube was inserted to the left open chest, between the central side of thorax descending aorta and the peripheral side thereof to produce an extracorporeal bypass. Blood flow rate was 80 ml/min, and blood flow bypassing was carried out for 2 days. In the tube of this Example, there was seen no thrombus formed at all. An electron microscopic observation also found only slight adsorption of platelets.

EXAMPLE-11

Example-7 was repeated except that a ethylene glycol/propylene glycol copolymer (4:6; molecular weight: 2,600) was used as the second component.

In the case of this Example, the result of Lee-White test was 83 minutes, and can be said it has excellent antithrombogenic properties.

EXAMPLE-12

Example-9 was repeated except that chondroitin was used as the second component.

In the case of this Example, the result of Lee-White test was 83 minutes, and can be said this has excellent antithrombogenic properties.

EXAMPLE-13

Propylene glycol (molecular weight: 4,000) was used as the second component, and polyether polyurethane in Example-1 was used as the first component. Solvent was tetrahydrofuran. As the third component, a mixture (9:1) of dimethyldimethoxysilane and tetramethoxysilane was used.

A mixture (2:1) of tetrahydrofuran and dioxane, the first component, the second component and the third component were mixed in the proportion of 100 parts, 11 parts, 3 parts and 5 parts, respectively, and, in the state of homogeneous mix, 1 part of water was added, and the mixture was stirred at 30° C. for 2 days. The solution was a transparent viscous liquid.

In the same manner as in Example-2, this solution was coated in a sack type blood pump made of polyvinyl chloride and having an inner volume of 76 ml to effect sufficient condensation of polysiloxane. The pump was tested as a ventricular assist pump of a goat, with a low feed of 0.8 ml/min for 3 weeks. There was formed no thrombus at all in the pump.

In a control wherein only the first component was applied to a blood pump, formation of thrombi was partly seen after 1 week in the sack portion of the pump.

EXAMPLE-14

Polyhydroxyethyl methacrylate and polyvinyl pyrrolidone were used as the second component, and polyether polyurethane in Example-1 was used as the first component. Solvent was tetrahydrofuran. As the third component, a mixture (9:1) of dimethyldimethoxysilane and tetramethoxysilane was used.

A mixture (2:1) of tetrahydrofuran and dioxane, the first component, the second component and the third component were mixed in the proportion of 100 parts, 11 parts, 3 parts and 5 parts, respectively, and, in the state of homogeneous mix, 1 part of water was added, and the mixture was stirred at 30° C. for 2 days. The solution was a transparent viscous liquid. Following Example-2, the solution was coated in a sack type blood pump made of polyvinyl chloride and having an inner volume of 76 ml to effect sufficient condensation of polysiloxane. The pump was tested as a left ventricular assist pump of a goat, with a low flow of 1.1 ml/min for 6 weeks. There was formed no thrombus at all in the pump.

In a control wherein only the first component was applied to a blood pump, formation of thrombi was partly seen after 1 week at the sack portion of the pump.

EXAMPLE-15

An experiment was carried out in the quite same manner as in Example-1 except that a polyethylene oxide/polydimethylsiloxane/polyethylene oxide block copolymer of the following formula was used.

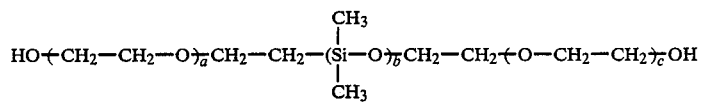

wherein $(a+c):b=0.68:0.32$; molecular weight: 5,600. The clotting time according to Lee-White test was found to be 98 minutes.

EXAMPLE-16

An experiment was carried out in the same manner as in Example-9 except that a mixture (80:20) of polyvinyl pyrrolidone (molecular weight: 36,000) and 2-acrylamide-2-methylpropane sulfonic acid was used as the second component, to reveal that the clotting time according to Lee-White test was 98 minutes.

What is claimed is:

1. An antithrombogenic material having an interpenetrating polymer network which comprises
   (1) a polyether type polyurethane or polyurethane urea containing in its main chain a segment comprising polytetramethylene oxide;
   (2) a water soluble polymer, a water swellable polymer or a combination thereof; and
   (3) a room temerpature cross-linking type silane coupling agent capable of being activated by water and induced condensation polymerization with cross-linking which is crosslinked to form a hydrophobic highly crosslinked polysiloxane network in which network the polyether type polyurethane or polyurethane urea, and the water soluble polymer, the water swellable polymer or combination thereof, are entangled.

2. The composition having antithrombogenic properites as claimed in claim 1, wherein said polymer is a macromolecular compound containing in its backbone, polyalkylene oxide wherein the carbon atom number of alkylene is 2 or 3 or 2 and 3.

3. The composition having antithrombogenic properties as claimed in claim 2, wherein the macromolecular compound containing in its main chain said polyalkylene oxide is a polyether polyurethane comprising polyethylene oxide as a segment.

4. The composition having antithrombogenic properties as claimed in claim 1, wherein the said polymer is a polydimethylsiloxane/polyethylene glycol copolymer.

5. The composition having antithrombogenic properties as claimed in claim 1, wherein the second component is at least one selected from polyvinyl alcohol, polyvinyl pyrrolidone, polyacrylic acid or a salt thereof, polyhydroxyethyl acrylic acid or a salt thereof, atelo collagen, water soluble gelatin, chondroitin sulfuric acid or a salt thereof, hyaluronic acid, alginic acid, water soluble or, oxydized starch (dialdehyde starch, diacetone acrylamide, 2-acrylamide-2-methylpropane sulfonic acid or a salt thereof, and soluble heparin.

6. The composition having antithrombogenic properties as claimed in claim 1, wherein the silicon-coupling agent is at least one selected from methyltriethoxysilane, methyltriacetoxysilane, tetramethoxysilane and tetraacetoxysilane.

7. A blood contact medical device characterized in that it comprises a blood contact surface constituted of a polyurethane or polyurethane urea having polytetramethylene oxide in its main chain, a water soluble and/or water swellable macromolecules, and a polysiloxane having crosslinked structure.

8. The composition having antithrombogenic properites as claimed in claim 1 wherein said silane coupling agent contains Si-OCOR or Si-OR wherein R is $CH_3$, $C_2H_5$, $C_3H_7$ or $C_4H_9$, as functional groups.

9. The composition having antithrombogenic properties as claimed in claim 1 wherein said silane coupling agent contains SiOX or SiX wherein X is halogen, as functional group.

10. The compositon having antithrombogenic properties as claimed in claim 9 wherein X is chlorine or bromine.

11. The composition having antithrombogneic properties as claimed in claim 1 wherein said silane coupling agent contains Si-$NR_2$ wherein R is $CH_3$, $C_2H_5$, $C_3H_7$ or $C_4H_9$ as functional groups.

12. The composition of claim 5 wherein the coupling agent is methyltriethoxysilane, methyltriacetoxysilane, tetramethoxysilane or tetraacetoxysilane.

13. The composition of claim 12 wherein said polyether type polyurethane is used.

14. The composition of claim 12 wherein said polyurethane urea is used.

* * * * *